United States Patent
Petzel et al.

(10) Patent No.: US 8,816,063 B2
(45) Date of Patent: Aug. 26, 2014

(54) NUCLEIC ACID PURIFICATION METHOD

(75) Inventors: Jan Petzel, Hilden (DE); Holger Wedler, Hilden (DE); Roland Fabis, Hilden (DE)

(73) Assignee: Qiagen GmbH, Hilden (DE)

( * ) Notice: Subject to any disclaimer, the term of this patent is extended or adjusted under 35 U.S.C. 154(b) by 67 days.

(21) Appl. No.: 13/319,855

(22) PCT Filed: May 11, 2010

(86) PCT No.: PCT/EP2010/002875
§ 371 (c)(1),
(2), (4) Date: Dec. 15, 2011

(87) PCT Pub. No.: WO2010/130402
PCT Pub. Date: Nov. 18, 2010

(65) Prior Publication Data
US 2012/0077969 A1    Mar. 29, 2012

(30) Foreign Application Priority Data

May 12, 2009 (EP) ..................................... 09160078
Jun. 3, 2009 (EP) ..................................... 09007338

(51) Int. Cl.
*C07H 21/00* (2006.01)
(52) U.S. Cl.
USPC ..................... 536/25.41; 536/25.4; 536/25.42
(58) Field of Classification Search
None
See application file for complete search history.

(56) References Cited

U.S. PATENT DOCUMENTS

2005/0130196 A1   6/2005   Hofstadler et al.

FOREIGN PATENT DOCUMENTS

| WO | 99 29703 | 6/1999 |
| WO | 00 69872 | 11/2000 |
| WO | 02 48164 | 6/2002 |
| WO | 2006 128776 | 12/2006 |

OTHER PUBLICATIONS

International Search Report issued Jul. 29, 2010 in corresponding Application No. PCT/EP2010/002875.
Johnson et al., "'Factory-Proof' Long PCT Enrichment and Amplicon Equalization for Next-Generation Resequencing Applications," 2008, Invitrogen, Retrieved from internet—URL: https://www.invitrogen.com/etc/medialib/en/filelibrary/Nucleic-Acid-Aplification-Expression-Profiling/PDFs.Par.12017.File.dat/O-076831_SequalPrep%20Application%20Note%201_0508.pdf (XP002570305).

*Primary Examiner* — Patrick Lewis
(74) *Attorney, Agent, or Firm* — Miles & Stockbridge, PC (57) ABSTRACT

The present invention relates to a method for purifying a defined amount of nucleic acids from a nucleic acid-containing sample, which has at least the following steps: (a.) contacting the nucleic acid-containing sample with a defined amount of a nucleic acid binding phase with the following features: (i) the nucleic acid binding phase has nucleic acid binding ligands that have at least one protonatable group; (ii) the nucleic acid binding ligands are bound to a carrier; (iii) the nucleic acid binding phase has a surface with a low charge density, wherein the amount of nucleic acids in the sample exceeds the binding capacity of the amount of nucleic acid binding phase used; (b.) binding of the nucleic acids to the nucleic acid binding phase at a pH (binding pH) that is below the pKs value of at least one of the protonatable groups; (c.) elution of the nucleic acids at a pH that is above the binding pH, wherein a defined amount of nucleic acids is obtained. Furthermore, corresponding kits and nucleic acid binding phases, which can be used for the purification of nucleic acids, are disclosed.

17 Claims, 6 Drawing Sheets

Agarose gel 1) 1µl LR-PCR06
2) 10µl eluate sample 1
3) 10µl eluate sample 2
4) 10µl eluate sample 3
5) 10µl eluate sample 4
6) 2µl HML

Agarose gel of the eluates (lane 1, 2μl HML; lanes 2-13, 10μl eluate LR-PCR1 to 12; lane 14, 5μl Lambda HindIII

NUCLEIC ACID PURIFICATION METHOD

CROSS REFERENCE TO RELATED APPLICATIONS

This application is a §371 National Stage Application of PCT/EP2010/002875, filed May 11, 2010, which claims priority to EP09160078.3, filed May 12, 2009; and EP09007338.8, filed Jun. 3, 2009.

BACKGROUND OF THE INVENTION

1. Field of the Invention

The present invention relates to a method for purifying a defined amount of nucleic acids from a sample containing nucleic acids. Furthermore, suitable kits and nucleic acid binding phases are provided, which allow a defined amount of nucleic acids to be isolated from a sample and are therefore suitable for normalizing the nucleic acid concentration in the eluate.

2. Description of Related Art

Various methods for purifying and isolating nucleic acids are known in the prior art. These include the use of phenol-chloroform, salting-out techniques, the use of ion exchangers and silica particles. A known method of nucleic acid purification is the so-called "charge-switch method". According to this, a nucleic acid binding phase at a first pH is brought into contact with a nucleic acid-containing sample, wherein the nucleic acid binding phase has a positive charge. This promotes binding of the negatively charged nucleic acids to the phase. For release/elution of the nucleic acids, according to the charge-switch principle a second pH is established, which is higher than the pKs value of the nucleic acid binding phase, in order to invert, i.e. neutralize, the positive charge. This promotes detachment of the bound nucleic acids from the nucleic acid binding phase.

For many analytical techniques and biological methods it is necessary to use a certain, i.e. defined amount of nucleic acid. The amount of nucleic acid isolated or amplified from different starting materials (samples) depends on a number of factors that are difficult to control, so that yields can vary widely depending on method and material. For subsequent experiments with the isolated nucleic acids to be carried out under comparable conditions, as a rule this requires quantification of the nucleic acid obtained and then adjustment of the concentrations or amount of nucleic acid to a specified value and therefore normalization. For many standardized processes and in particular process automation, such normalization is often essential, in order to obtain reproducible results.

For this reason there are a large number of methods for quantifying nucleic acids in a purified sample. One example of a usual quantification method is the spectrophotometric determination of the amount of DNA in a sample. Following determination of the concentration of the nucleic acid in the sample, the concentration can then be adjusted uniformly. Other known methods for quantifying nucleic acids are based on intercalating dyes, e.g. ethidium bromide, SYBR Green or Picogreen. The concentration can be determined by comparing the measured values with a standard curve.

In addition to the spectrometric or fluorescence-based quantification techniques described, various purification techniques are also known in the prior art, which are said to allow uniform concentrations of nucleic acids to be prepared from different starting materials. Examples are the MagneSil-Kit from Promega or the SequalPrep-Kit from Invitrogen.

The MagneSil-Kit from Promega is used, for example, for isolating genomic DNA from whole blood. The kit is based on the binding of DNA to silica-coated paramagnetic particles under chaotropic salt conditions. As a result, usually 1 μg (±50%) of purified genomic DNA is obtained after elution with a low-salt buffer or water. Due to the relatively large fluctuations of up to 50%, this method requires improvement.

The SequalPrep-Kit from Invitrogen is based on binding of DNA to surfaces that are coated with an ion exchanger. The DNA binds at an acid pH and elution is carried out with a strongly alkaline buffer, the pH of which is above the pKs value of the ion exchanger. This kit is based on the so-called charge-switch technology (see above). The kit finds application in the purification and normalization of long range (LR) PCRs and it is also suitable for template preparation for sequencings. The manufacturer states yields of approx. 25 ng with a two to three-fold fluctuation when using at least 250 ng starting DNA. This means that also here the fluctuations can also be relatively large, so that once again optimization is required.

The known purification techniques therefore in practice still have wide variations in yields. Difficulties arise in particular when different amounts of starting material or different starting materials are used.

SUMMARY

Apart from obtaining a purified nucleic acid, it is therefore desirable, during isolation, also to purify a defined amount of nucleic acids and thus already obtain, for a sample material, an eluate that has, between different samples, an almost identical concentration of nucleic acids with the lowest possible fluctuations in concentration.

Furthermore, it is desirable for the purified nucleic acids to be immediately ready for use in further applications, i.e. for example no further rebuffering or the like is necessary. This is not always possible based on the purification techniques known in the prior art, as these often necessitate high pH values and/or high salt concentrations for elution of the purified nucleic acids. Therefore it is often necessary to precipitate the purified nucleic acid beforehand or else for example to adjust the pH for the subsequent applications (downstream applications), as a result of which, however, the concentration in the eluate may change again.

Even if the known techniques are suitable for purification of nucleic acids and with certain reservations also for the purification of a defined amount of nucleic acids, the existing methods need to be improved, in particular to allow purification of a defined amount of nucleic acids from different samples, with only small fluctuations in the concentration of the purified nucleic acid.

Therefore the problem underlying the present invention is to improve the existing methods for respectively purifying nucleic acids.

The present invention solves this problem with a method for isolating and/or purifying a defined amount of nucleic acids from a nucleic acid-containing sample, which has at least the following steps:
  a. contacting the nucleic acid-containing sample with a defined amount of a nucleic acid binding phase with the following features:
     (i) the nucleic acid binding phase has nucleic acid binding ligands that have at least one protonatable group;
     (ii) the nucleic acid binding ligands are bound to a carrier,
     (iii) the nucleic acid binding phase has a surface with a low charge density, wherein the amount of nucleic acids in the sample exceeds the binding capacity of the nucleic acid binding phase used;

b. binding of the nucleic acids to the nucleic acid binding phase at a pH (binding pH) that is below the pKs value of at least one of the protonatable groups;

c. elution of the nucleic acids at a pH that is above the binding pH, wherein a defined amount of nucleic acids is obtained.

DETAILED DESCRIPTION OF A PREFERRED EMBODIMENT

The present invention relates to the isolation and/or purification of nucleic acids by means of a special nucleic acid binding phase, which permits the purification/isolation of a defined amount of nucleic acids from a sample with small fluctuations of concentration. The design of the nucleic acid binding phase is decisive for this. For binding the nucleic acids from the sample, the latter has nucleic acid binding ligands, which have at least one protonatable group. Suitable protonatable groups, in particular amino groups, are described in detail below. The binding of the nucleic acids takes place at a pH below the pKs value of at least one of these protonatable groups. The protonatable groups take up one or more protons and thereby become positively charged, which means that the nucleic acid binding phase can bind the negatively charged nucleic acids. Elution occurs at a higher pH, so that the positive charge of the protonatable group becomes smaller and the nucleic acid bound to the nucleic acid binding phase is released. According to some embodiments, the protonatable group can even be neutrally or optionally also negatively charged during elution. The method can be used for isolating and/or purifying nucleic acids from a biological sample. Furthermore, the method can be carried out following a classical nucleic acid purification technique, in order for example to normalize already purified nucleic acids and thus obtain a defined amount of nucleic acids.

An essential feature of the present invention is the surface of the nucleic acid binding phase. According to the invention, this has a low charge density. This special surface, in combination with the feature that the amount of nucleic acids in the sample exceeds the binding capacity of the amount of nucleic acid binding phase used, surprisingly has the effect that a defined amount of nucleic acids can be isolated from the sample, wherein far smaller fluctuations in nucleic acid concentration occur, compared with the prior art.

In contrast to the prior art, according to the invention there is no attempt to achieve a surface that allows the binding of an especially large amount of nucleic acids. Rather, the charge density on the surface and therefore the nucleic acid binding capacity of the nucleic acid binding phase are intentionally reduced. Therefore only a limited amount of nucleic acids, but always identical i.e. defined for a particular sample, can be bound and accordingly eluted. For a particular biological sample material, therefore advantageously the binding capacity of the nucleic acid binding phase must be determined only once. Further quantification steps can be omitted, as a specified amount of nucleic acid binding phase can only bind a defined and therefore always identical amount of nucleic acid. As a result, advantageously processing steps such as concentration or dilution of the purified samples can be omitted, which would otherwise be necessary for adjusting all the samples to the same concentration of purified nucleic acids.

The term "a defined amount" refers in particular to a concentration of nucleic acids that is within a defined, i.e. narrow range of variation. When the latter is not known for a particular sample or sample material, the range of variation can be determined (experimentally). Preferably the nucleic acid amounts or concentrations achieved with the method according to the invention are in a narrow range, so that, depending on sample material, the variations are less than ±30%, preferably less than ±20% and in particular in the region of ±15% and especially preferably ±10%.

The amount of the nucleic acid binding phase in relation to the amount/concentration of nucleic acids in the sample material should preferably be selected so that it is always in the plateau region and therefore in the saturation region of the nucleic acid binding capacity of the nucleic acid binding phase. Therefore the amount of nucleic acid binding phase (for example the amount of particles or the size of carrier surface coated with nucleic acid binding ligands) is selected so that the nucleic acids in the sample are in excess to the nucleic acid binding capacity of the amount of nucleic acid binding phase used. Owing to the small nucleic acid binding capacity of the nucleic acid binding phase according to the invention, the method according to the invention has clear advantages over the use of nucleic acid binding phases/particles that have a high nucleic acid binding capacity (for example silica particles or particles coated conventionally with polyamines). In the prior art, either high fluctuations in the yield of nucleic acids must be accepted, or such small amounts of nucleic acid binding phase/particles must be used, so that handling becomes difficult, especially within the context of an automated process. For example, when using the particles known in the prior art, the amount used would have to be diluted to such an extent that they would be difficult to handle in an automated process. This in its turn has sources of error, as the loss of even a few particles with high nucleic acid binding capacity would result in a marked fluctuation in yield of nucleic acids. Therefore according to these aspects as well, the method according to the invention is superior to the prior art.

For purification of a defined amount of nucleic acids and therefore normalization of the nucleic acid concentration, according to the invention the nucleic acid binding phase is offered so much nucleic acid that the nucleic acid binding capacity of the nucleic acid binding phase used is exhausted. The remaining, unbound proportion of the nucleic acid is discarded during purification. Optionally the nucleic acid binding phase with the bound nucleic acid can be washed prior to elution. In the elution step, the nucleic acid is transferred from the surface of the nucleic acid binding phase to the eluting solution. As a result, for a given sample material, always the same, i.e. defined amount of nucleic acid is obtained during purification.

Preferably, the surface with low charge density is achieved by one or more of the following features:

a. the nucleic acid binding ligands have, bound on the carrier, in each case not more than one or two protonatable groups for binding the nucleic acids; and/or b. the nucleic acid binding ligands are selected from the group of mono- and diamines; and/or c. the carrier is coated with a mixture of nucleic acid binding ligands and diluting ligands; and/or d. the nucleic acid binding ligands bound to the carrier are in deficit.

Figure 1:
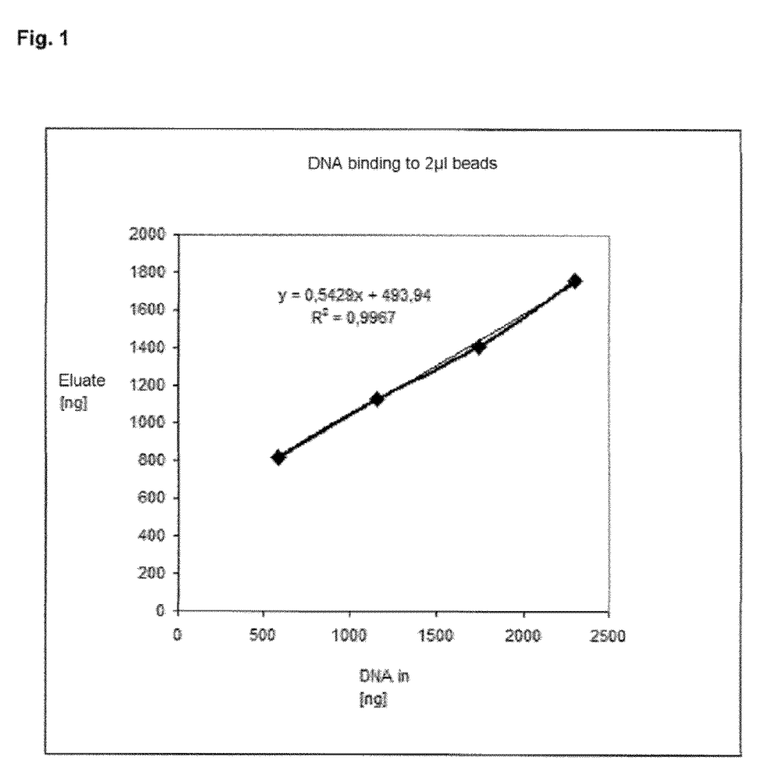
FIGS. 1-8 depict embodiments of the present invention.

According to the invention, as described, a nucleic acid binding phase is used that has a surface with low charge density. For this, the nucleic acid binding ligands preferably have in each case not more than one or two protonatable groups, for example amino groups, for binding the nucleic acids. Correspondingly, the nucleic acid binding ligands are preferably selected from the group of mono- and diamines. It has been found that in contrast to conventional coating with polyamines such as spermine and spermidine, mono- and/or diamines are very suitable for normalizing nucleic acid concentrations. Carriers coated conventionally with polyamines apparently have a charge density on the surface that is too high to be suitable for normalization. Therefore they bind larger amounts of nucleic acids. If such a surface is brought into contact with a nucleic acid-containing sample, it is found that the binding capacity is strongly dependent on the nucleic acid concentration. Typically, in the range investigated, there is a proportional relationship between offered and eluted amount of DNA. FIG. 1 shows this behavior for the example of polymer particles coated with the polyamine spermine, which leads to the described variations in the amount of purified nucleic acid, so that normalization during purification is not possible. The mono- and/or diamines that are preferably used can be applied either individually or as a mixture.

By using preferably mono- and/or diamines for coating the carrier, in contrast a limited, but defined amount of charge carriers, and therefore nucleic acid binding groups, is produced on the surface. The resultant charge carrier density for binding nucleic acids is far lower than with corresponding coating with polyamines, e.g. spermine or even polyethyleneimines. In particular, polymer particles modified with N-propyl-1,3-propanediamines are very suitable for normalizing the nucleic acid concentration already during purification and thus for isolating a defined amount of nucleic acids from a sample. The advantage of a carrier coated with monoamines or diamines for preparation of a nucleic acid binding phase is in particular that only a limited amount of nucleic acid is bound, but within a small range of variation said amount is the same for a particular sample. Through the high reproducibility in preparation of the carrier materials and in the amino functionalization of the carrier surface, a narrow variability of the charge carrier density and hence of the nucleic acid binding capacity is achieved. As a result, undesirable fluctuations in nucleic acid concentration are avoided during purification. The advantages described can be demonstrated not only relative to polyamines, but are also found in particular relative to the silica particles that are usually employed, for which, owing to the high nucleic acid binding capacity of the surface, fluctuations of up to 50% occur during isolation of the nucleic acids from the same sample material.

Surprisingly, it was also found that a lower charge density on the surface of the carrier can also be achieved in that if for example polyamines are used as nucleic acid binding ligands, the carrier is coated with only a small amount of polyamines, to obtain the desired low charge density on the surface of the nucleic acid binding material. According to one embodiment, the nucleic acid binding ligands are therefore arranged at a distance from one another on the carrier material, or diluted. In order to achieve such an arrangement of the nucleic acid binding ligands, according to one embodiment the carrier can be coated with only small amounts of nucleic acid binding ligands, for example polyamines or preferably mono- and/or diamines. Preferably, the functionalization with nucleic acid binding ligands therefore takes place in deficit especially in relation to the binding capacity of the carrier material surface. As a result, as it were, a dilution of the nucleic acid binding ligands on the carrier is achieved, so that fewer protonatable groups are available. For example, only 50%, 25%, 10% or only 5% of the functional groups or groups functionalizable with the nucleic acid binding ligands on the carrier material are functionalized with nucleic acid binding ligands. Once again, a nucleic acid binding phase with a low charge density is obtained on the surface.

Moreover, the carrier can be coated with a mixture of nucleic acid binding ligands and so-called diluting ligands. The term "diluting ligands" is used here to represent the function in relation to the nucleic acid binding ligands. Their function is to allow the amount of nucleic acid binding ligands on the carrier to be varied and thus adjusted so that a lower charge density can be established on the surface of the nucleic acid binding phase. The higher the proportion of diluting ligands relative to the nucleic acid binding ligands, the fewer nucleic acid binding ligands are applied on the carrier and the lower is the nucleic acid binding capacity. The diluting ligands can be charged negatively, positively or neutrally or can have ionizable groups. According to one embodiment the diluting ligands do not bind any nucleic acids or they bind the nucleic acids with a lower affinity than the nucleic acid binding ligands. If the diluting ligands bind nucleic acids, they bind them according to one embodiment with an affinity that is at least 20%, at least 50% or at least 75% lower than the affinity of the nucleic acid binding ligands. The proportion of nucleic acid binding ligands relative to the dilution groups can be for example ≤50%, ≤25%, ≤10% or only ≤5%. Suitable diluting ligands are for example dimethylamine, diethylamine and ammonia or diluting ligands having groups of formula R, —OH or —OR, where R is a linear or branched alkyl residue. Another example of a suitable diluting ligand would be ethanolamine. According to a preferred embodiment, a mixture of nucleic acid binding ligands and diluting ligands is used for coating the carrier.

The binding capacity of the nucleic acid binding phase is according to one embodiment in the range from 1 to 500 µg nucleic acid per mg nucleic acid binding phase, wherein smaller binding capacities such as 1 to 300 µg, 1 to 200 µg, 10 to 100 µg nucleic acid per mg nucleic acid binding phase, in particular DNA, are also possible. According to a preferred embodiment, the binding capacity of the nucleic acid binding phase is 0.01 to 100 µg, 0.025 to 100 µg, 0.05 to 100 µg or 0.1 to 100 µg nucleic acid per mg nucleic acid binding phase, preferably 0.01 to 50 µg, 0.025 to 50 µg, 0.05 to 50 µg or 0.1 to 50 µg nucleic acid per mg nucleic acid binding phase and especially preferably 0.01 to 10 µg, 0.025 to 10 µg, 0.05 to 10 µg or 0.1 to 10 µg nucleic acid per mg nucleic acid binding phase. These nucleic acid binding phases are suitable in particular for normalizing even smaller amounts of nucleic acids—especially when small volumes are being handled.

In order to achieve gentle elution of the nucleic acids, elution is preferably carried out at a pH that is above the binding pH, but is at least one pH unit, preferably at least two pH units below the pKs value of at least one of the protonatable groups, preferably all protonatable groups. This has the considerable advantage that elution can also be carried out in gentle conditions. The present invention therefore permits elution at a pH that is below the pKs values of the protonatable groups.

According to one embodiment of the present invention, binding of the nucleic acids takes place at a pH from 3 to 8. This statement refers to the pH during binding and thus in the sample. The method according to the invention can, depending on the form of the solid phase, also be carried out in very gentle conditions, so that the binding of the nucleic acids can also be carried out at a pH from 4 to 7.5; preferably at 5 to 7.5; especially preferably at 5 to 7 and quite especially preferably at 6.5 to 7 and thus in the almost neutral region. Since the protonatable groups preferably have a pKs value from 9 to 12, more preferably from 10 to 12, even at relatively neutral pH these are sufficiently positively charged to permit effective binding of the nucleic acids. Therefore binding can take place under very gentle conditions, which avoids damaging the nucleic acids.

Furthermore, it has proved advantageous for binding to be carried out at a low salt concentration. According to one embodiment, the salt concentration during binding of the nucleic acids to the nucleic acid binding phase is therefore M. The salt concentration is preferably ≤0.5 M, ≤0.25 M or even ≤0.1 M. A low salt concentration is preferable for optimizing the binding of the nucleic acids to the solid phase. Excessively high ion concentrations can adversely affect the ionic interactions of nucleic acid and of the nucleic acid binding phase. It has been found that the binding buffer can also contain certain amounts of organic substances, for example carbohydrates, alcohols (for example ethanol, methanol), acetone, acetonitrile or mixtures thereof. These do not have an adverse effect on binding.

Another important step of the present method is elution of the nucleic acids. As already mentioned, nucleic acid release takes place at a pH that is above the binding pH. As a result, during elution the protonatable groups are less positively charged, which is favorable for release of the nucleic acids. Furthermore, the pH during elution is preferably at least one pH unit below the pKs value of at least one of the protonatable groups of the nucleic acid binding phase. As explained above, this has the result that elution can be carried out under particularly gentle conditions.

Depending on the nucleic acid binding ligands or nucleic acid binding phase used, elution preferably takes place at a pH from 7.5 to 11, from 7.5 to 10, preferably at a pH from 8 to 9, respectively 8.2 to 8.8. Particularly advantageous results are achieved at these pH values, as release of the nucleic acids is particularly gentle.

In order to allow direct further processing of the isolated nucleic acids in the eluting solution, preferably in an elution buffer, this preferably has a low salt concentration. Therefore, according to one embodiment, the salt concentration is ≤1 M, preferably ≤0.5 M, ≤0.25 M, ≤0.1 M, especially preferably ≤50 mM, ≤25 mM or even ≤10 mM. Suitable salts are halides, in particular chlorides, of the alkali metals and alkaline-earth metals or ammonium, other salts of mineral acids, acetates, borates and compounds such as Tris, Bis-Tris and based on organic buffers, for example MES, CHAPS, HEPES and the like. Suitable substances for elution are, moreover, known from the prior art.

Especially in vacuum-based or centrifugation-based elution of the nucleic acids, for example when using a nucleic acid binding membrane or when using nucleic acid binding particles in combination with a membrane, which serves as a barrier to the particles, it may be advantageous, especially with small elution volumes, if additional measures are taken to ensure that within small fluctuations the same elution volume is also achieved in each case—especially when working with multiple batches, for example a 48-well or 96-well plate. Thus, it has provided advantageous to add at least one hydrocarbon to the eluting solution. In this way, advantageously a more uniform eluate volume is obtained. This is presumably because the stacked layer of hydrocarbon promotes complete penetration of the eluting solution through the membrane, so that a more uniform eluate volume is obtained. The hydrocarbon and/or the mixture of hydrocarbons can have one or more of the following features:
a) the hydrocarbon is an unsubstituted or substituted alkane;
b) the hydrocarbon is a water-immiscible alkane;
c) the hydrocarbon is an acyclic alkane;
d) the hydrocarbon is an unbranched acyclic alkane;
e) the hydrocarbon is a branched acyclic alkane;
f) the hydrocarbon is a cyclic alkane;
g) the hydrocarbon is an alkane with 6 to 16 carbon atoms;
h) the hydrocarbon is an alkane with 8 to 12 carbon atoms;
i) the hydrocarbon is an alkane that is selected from the group n-octane, n-nonane, n-decane and n-dodecane; and/or
j) the hydrocarbon is preferably a mineral oil.

To promote purification, preferably at least one washing step is carried out after binding and prior to elution of the nucleic acids. Aqueous solutions with low salt concentrations, but also water, are preferred for washing. If salts are contained in the washing buffers or washing solutions, they are preferably at a concentration of ≤400 mM, especially preferably of ≤200 mM, ≤100 mM, ≤50 mM and/or even ≤25 mM. Organic constituents may be present in the washing buffer, for example alcohols, polyols, polyethylene glycols, acetone, acetonitrile, carbohydrates or mixtures thereof. The washing buffers or washing solutions can, however, be without disturbing amounts of the corresponding organic constituents, so that subsequent applications, for example enzymatic processing, amplification reactions and the like ("downstream" applications) are not hampered.

The nucleic acid binding ligands are linked to the carrier covalently or noncovalently by electrostatic, polar or hydrophobic interactions. Preferably this takes place within the context of a coating operation. If the carrier material does not have any suitable functional groups for binding the nucleic acid binding ligands, a functionalization of the carrier material can take place first, to provide it with suitable functional groups, in particular carboxyl groups. The corresponding profile of coating of the carrier material with nucleic acid binding ligands in deficit can also be achieved by providing the carrier material correspondingly with fewer functional groups for binding the nucleic acid binding ligands. Suitable coating techniques are known in the prior art and therefore do not require more detailed description. Binding of the nucleic acid binding ligands to the carrier and in particular to the functional groups of the carrier can take place in various ways. The nucleic acid binding ligands can, for example in the case of di- or polyamines, be bound via an amino group. The nucleic acid binding ligands can, however, also have a functional group, which is utilized for binding to the carrier. Suitable functional groups are known in the prior art. Moreover, there is also the possibility of linking the nucleic acid binding ligands directly to the surface of the carrier, preferably to the surface of a polymer carrier. This can for example take place directly via the carbon backbone.

Preferred protonatable groups, which have proved suitable for binding nucleic acids, are amino groups; primary, secondary and tertiary amino groups are preferred. The protonatable groups, such as in particular the amino groups, preferably have a pKs value of at least 8. The pKs value is preferably 9 to 12, more preferably 10 to 12. The nucleic acid binding ligands preferably have 1 to 2 amino groups. Preferred nucleic acid binding ligands are for example primary, secondary and tertiary mono- and diamines. These can be substituted or unsubstituted.

Preferred examples of nucleic acid binding ligands are in particular primary, secondary and tertiary amines of the formulas
(a) $R_3N$
(b) $R_2NH$
(c) $RNH_2$ and/or
(d) $X—(CH_2)_n—Y$ with $X=R_2N$, $RNH$ or $NH_2$ and $Y=R_2N$ or $RNH$ or $NH_2$ wherein
R=independently of one another, a linear, branched or cyclic alkyl, alkenyl, alkynyl or aromatic substituent, wherein the latter can also contain one or more heteroatoms;
n=0 to 20
N-Propyl-1,3-propanediamine is preferably used as nucleic acid binding ligand.

Furthermore, cyclic amines, aromatic amines or amino functionalized heterocycles can also be used. The amines can carry substituents, for example alkyl, alkenyl, alkynyl or aromatic substituents, furthermore the hydrocarbon chains can also be closed, forming a ring. The hydrocarbon chains can also have heteroatoms, such as oxygen, nitrogen, sulfur or silicon, or branchings. The amino groups of the amines preferably have pKs values from 9 to 12, especially preferably from 10 to 12.

Further suitable nucleic acid binding ligands are polyoxyalkylene amines with one, two or three amino groups. These are for example polyoxylalkylene amines obtainable under the name "Jeffamines". Jeffamines contain primary amino groups, which are bound to the terminus of the polyether backbone. The polyether backbone can be based on propylene oxide, ethylene oxide or mixtures thereof; the use of other backbone segments is also conceivable.

Also mixtures of the corresponding nucleic acid binding ligands can be used according to the invention or can be applied on a carrier.

Preferably the amino groups of the nucleic acid binding ligands are not conjugated with an electron density-lowering group, for example a carboxyl group, a carbonyl group, a group with C—C double bonds or a β-hydroxyethyl group, so that their pKs value is preferably between 9 and 12. Conjugation with an electron density-lowering group is deemed to be present when an amino function and the corresponding electron density-lowering group are connected via only three, two or fewer carbon atoms.

Possible carriers for the nucleic acid binding ligands are for example organic polymers such as polystyrene and derivatives thereof, polyacrylates and polymethacrylates, and derivatives thereof or polyurethanes, nylon, polyethylene, polypropylene, polybutylene, and copolymers of these materials. Furthermore, these nucleic acid binding ligands may also be coupled to polysaccharides, in particular hydrogels such as agarose, cellulose, dextran, Sephadex, Sephacryl, chitosan. Moreover, the nucleic acid binding ligands may also be bound to inorganic carriers such as e.g. glass or further metal oxides and metalloid oxides (in particular oxides of formula MeO, wherein Me is preferably selected from the group comprising Al, Ti, Zr, Si, B, in particular $Al_2O_3$, $TiO_2$, silica and boron oxide) or metal surfaces, e.g. gold. Preferably the carrier material does not have any nucleic acid binding capacity of its own.

Magnetic particles are especially advantageous for manipulation. The nucleic acid binding phase is therefore preferably magnetic and can be paramagnetic, ferrimagnetic, ferromagnetic or superparamagnetic. Superparamagnetic or paramagnetic particles are preferred. The individual steps and embodiments for the manipulation of magnetic particles, as they are preferably used according to the invention, are well known in the prior art and therefore do not require detailed description.

The nucleic acid binding ligands can be bound to these carriers either directly or via spacers. They can also be part of a larger molecule. Examples of spacers are hydrocarbon chains, poylethylene glycols or polypropylene glycols, and functionalized silanes. These spacers can be linear or branched.

Acid amides or acid anhydrides, epoxides, tosyl groups, formyl groups, sulfonyl chlorides, maleimides or carboxylate groups activated with carbodiimide chemistry can be used as chemical functionalities for binding of the nucleic acid binding ligands. In the context of the invention, noncovalent binding of the nucleic acid binding ligands, for example amines, is also possible, e.g. by ionic interactions or by adsorption processes. The nucleic acid binding ligands can also be bound via thiols to e.g. gold surfaces. Binding of the nucleic acid binding ligands to carboxylated surfaces is preferred.

Further embodiments of suitable carrier materials for binding the nucleic acid binding ligands comprise nonmagnetic and magnetic particles, column materials, membranes, and surface coatings. We may further mention carriers such as tubes, membranes, fleece, paper, reaction vessels such as PCR vessels, Eppendorf tubes, multiplates, chips and microarrays. These carriers can be coated as described above with the nucleic acid binding ligands, to obtain a nucleic acid binding phase according to the invention. By the density and size of the area of said carrier material coated with nucleic acid binding ligands, once again a defined amount of a nucleic acid binding phase is made available for purification. For example, individual or all reaction zones (wells) of a microtiter plate or of a multiplate or of a corresponding device for processing samples can be coated completely or partially with the nucleic acid binding ligands, in order to obtain a nucleic acid binding phase.

Efficient elution and therefore detachment of the bound nucleic acids from the nucleic acid binding phase are particularly decisive for the efficiency of nucleic acid purification. It was found, surprisingly, that not only the pKs values of the protonatable groups of the nucleic acid binding ligands are decisive. The structure of the nucleic acid binding phase and the presence of other functional groups also contribute to promoting and improving elution at pH in the neutral or weakly alkaline range.

According to one embodiment, the nucleic acid binding phase additionally carries functional groups which promote the elution of nucleic acids at the elution pH, for example by exerting a repulsion effect at the elution pH. Preferably, therefore, these functional groups are negatively charged during elution. The pKs values of these groups can for example be in the range from 0 to 7, preferably 1 to 5. For example ion exchangers, in particular cation exchangers, preferably acidic groups, for example carboxyl groups, are suitable. Other suitable groups are betaines, sulfonates, phosphonates and phosphates. For example, the solid carrier can be functionalized with carboxyl groups, to permit binding of the nucleic acid binding ligands. During binding of the nucleic acid binding ligands, the concentration thereof can be selected so that some of the carboxyl groups are free and therefore are not functionalized with the nucleic acid binding ligands. At low pH values these do not hamper the binding of the nucleic acids. At higher pH, however, these are preferably negatively charged and thus promote detachment of the nucleic acids from the nucleic acid binding ligands. This interaction can be further promoted by selection of the length or of the distance between the protonatable groups of the nucleic acid binding ligands and the negatively ionizable groups, for example the carboxyl groups. Advantageously, this promotes elution at low pH, so that the yield increases. The choice, strength and length of the functional groups, which exert a repulsion effect on the nucleic acids at the elution pH, varies depending on the nucleic acid binding group selected, and so in particular the number of protonatable groups per nucleic acid binding group and their distance from the elution-promoting functional groups. According to one embodiment, the elution-promoting functional groups function as diluting ligands.

Through choice/combination of the parameters described, in particular of the elution-promoting functional groups, the diluting ligands, and dilution or mixing with nucleic acid binding ligands, the pH of the nucleic acid binding phase can be optimized for the elution conditions. The elution profile of the nucleic acid binding phase, in particular the elution pH, can be controlled or adjusted correspondingly.

Nucleic acids that can be purified using the method according to the invention can be present in body fluids such as blood, urine, stool, saliva, sputum, or other body fluids, in biological sources such as tissue, cells, in particular animal cells, human cells, plant cells, bacterial cells and the like, organs such as liver, kidney or lung etc. For this, the nucleic acid can be obtained from carrier materials such as swabs, PapSmears, and stabilizing media such as PreServCyt or Surepath, or also from other liquids, for example juices, aqueous samples or foodstuffs generally. Furthermore, the nucleic acids can be obtained from plant material, bacterial lysates, tissue embedded in paraffin, aqueous solutions or gels.

If the nucleic acid is present in a cell material, as is known in the prior art, the cell material can be disrupted and in particular can be lysed, in order to release the nucleic acids. Corresponding cell disruption techniques or lysis techniques are known in the prior art and therefore require no further description.

Owing to the fact that, in the method according to the invention, water-based buffers can be used and dangerous chemicals are obsolete, very clean eluates are achieved, which preferably do not contain any substances that constitute a disadvantage for the downstream applications, for example PCR, restriction digestion, transfection or sequencing reactions. Furthermore, with the method according to the invention it is possible to bind the nucleic acid under very gentle conditions, for example at pH 6.5-7 and to carry out elution at only slightly alkaline pH such as 8.5 and very low salt concentrations, for example 25 mmol Tris, so that no dilution or neutralization is necessary for further investigations and uses (downstream applications).

The standardized or normalized nucleic acid concentration according to the invention can preferably be used for an enzymatic reaction such as for example nucleic acid amplification, modification reactions or sequencing reactions. The nucleic acids that are purified and therefore normalized according to the invention are also suitable for example for short tandem repeat (STR), analyses and transfections, which also use defined amounts of nucleic acids.

Furthermore, the present invention relates to the use of a nucleic acid binding phase as described above for purifying a defined amount of nucleic acids from a sample and therefore for normalization of the nucleic acid concentration. The nucleic acid binding phase has nucleic acid binding ligands with at least one protonatable group, wherein the nucleic acid binding ligands present are bound to a carrier and the nucleic acid binding phase has a surface with a low charge density, wherein an elution pH is established that is above the binding pH and wherein the nucleic acids in the sample are present in excess to the binding capacity of the amount of nucleic acid binding phase used.

The low charge density is preferably achieved by one or more of the following features:
a) the nucleic acid binding ligands have, bound to the carrier, in each case not more than one or two protonatable groups for binding the nucleic acids; and/or
b) the nucleic acid binding groups are selected from the group of mono- and diamines; and/or
c) the carrier is coated with a mixture of nucleic acid binding groups and diluting groups; and/or
d) the nucleic acid binding ligands bound to the carrier are in deficit.

The nucleic acid binding phase, used according to the invention, in particular has nucleic acid binding ligands with at least one protonatable group, which has a pKs value of at least 8, preferably 9 to 12. Preferred embodiments are described above in detail (see above disclosure) and are characterized in particular by one or more of the following features:
a. the protonatable group(s) have a pKs value from 9 to 12, preferably a pKs value from 10 to 12; and/or
b. the protonatable groups are amino groups and are not conjugated with the electron density-lowering groups; and/or
c. the nucleic acid binding phase has functional groups that promote the release/elution of the nucleic acids at the elution pH, preferably cation exchangers, in particular carboxyl groups; and/or
d. the carrier has no nucleic acid binding properties of its own apart from the nucleic acid binding ligands; and/or
e. the carrier is selected from the group consisting of organic polymers such as polystyrene and derivatives thereof, polyacrylates and polymethacrylates and derivatives thereof, polyurethanes, nylon, polyethylene, polypropylene, polybutylene and copolymers of these materials, polysaccharides and hydrogels such as agarose, cellulose, dextran, Sephadex, Sephacryl, chitosan, inorganic carriers, glass or further metal oxides and metalloid oxides (in particular oxides of the formula MeO, where Me is preferably selected from the group comprising Al, Ti, Zr, Si, in particular $Al_2O_3$, $TiO_2$, silica), carriers with metal surfaces, e.g. gold, magnetic particles or mixtures thereof; and/or
f. the nucleic acid binding ligands are selected from the group consisting of primary, secondary and tertiary amines of the formulas
(a) $R_3N$
(b) $R_2NH$
(c) $RNH_2$ and/or
(d) $X-(CH_2)_n-Y$ with $X=R_2N$, RNH or $NH_2$ and $Y=R_2N$ or RNH or $NH_2$
wherein
R=independently of one another, a linear, branched or cyclic alkyl, alkenyl, alkynyl or aromatic substituent, wherein the latter can also contain one or more heteroatoms;
n=0 to 20,
and preferably represent mono- and diamines. These can be substituted or unsubstituted.

Moreover, the invention provides a kit for purifying a defined amount of nucleic acids, which uses a nucleic acid binding phase according to the invention. Details for the nucleic acid binding phase and the advantages with respect to normalization are described in detail above and also apply in connection with the kit according to the invention. Reference is made to the above disclosure.

The kit according to the invention preferably has at least one of the following features:
a. a binding buffer or a binding solution with a pH that is at least one pH unit below the pKs value of at least one of the protonatable groups of the nucleic acid binding phase, and/or a binding buffer that makes it possible to establish said pH in the sample; and/or
b. an elution buffer or an eluting solution with a pH that is one pH unit below the pKs value of at least one of the protonatable groups of the nucleic acid binding phase, and/or an elution buffer that makes it possible to establish said pH in the sample.

According to one embodiment, the kit has a binding buffer or binding solution that has at least one of the following features:
  i. a pH from 3 to 8; and/or
  ii. a pH from 4 to 7.5; and/or
  iii. a pH from 4.5 to 7; and/or
  iv. a pH from 5.5 to 7; and/or
  v. a pH from 6.5 to 7; and/or
  vi. a salt concentration of ≤1M, ≤0.5M, ≤25M or w≤0.1M.

Moreover, the kit can have an elution buffer or eluting solution that has at least one of the following features:
  i. a pH from 7.5 to 10; and/or
  ii. a pH from 8 to 9; and/or
  iii. a pH from 8.2 to 8.8; and/or
  iv. a salt concentration of ≤1M, ≤0.5M, ≤0.25M, ≤0.1M, ≤25 mM, ≤15 mM, mM or ≤10 mM; and/or
  v. it is selected from the group consisting of water, biological and organic buffer.

Details regarding the nucleic acid binding phase and the binding and elution conditions are described in detail above and also apply in connection with the kit according to the invention and characterize the constituents/buffers used therein. Reference is made to the above disclosure. Furthermore, the kit can contain further usual constituents, for example lysis, washing and/or neutralizing reagents or buffers.

The corresponding kits can in particular be used within the context of the method according to the invention and are suitable in particular for normalization. Therefore the kit according to the invention can be used in particular in automated systems.

The present methods, kits and nucleic acid-binding solid phases can be used in particular in the area of molecular biology, molecular diagnostics, in forensics, in food analysis and in Applied Testing. They are suitable in particular for automated use.

The eluted nucleic acids can preferably be further processed directly, and so are used for example in the context of molecular-biological applications such as for example enzymatic reactions, for example PCR, RT-PCR, restriction digestion, sequencing or transcription. Further purification is not necessary, provided the elution buffers are designed as described above and preferably have a low salt concentration.

Possible nucleic acids for purification include DNA and RNA, in particular genomic DNA, plasmid DNA, and PCR fragments, cDNA, miRNA, siRNA, as well as oligonucleotides and modified nucleic acids, for example PMA or LMA. Viral or bacterial RNA and DNA or nucleic acids from human, animal or plant sources can also be purified. Moreover, DNA/RNA hybrids may also be considered for purification according to the invention, to give just a few examples.

The present invention will be explained below with some examples. These are not limiting, but represent preferred embodiments of the present invention. Furthermore, all the references stated herein form part of the disclosure.

EXAMPLES

Long range (LR) PCR fragments (8 to 11 kb) were used as model systems in the experiments. The tests were performed on the basis of the following specifications.

FIG. 1 shows the dependence of the amount of DNA eluted (LR PCR fragments) on the starting amount of DNA, using spermine-coated polymer beads. The more DNA was offered to the particles coated with polyamines, the more DNA could be bound and then eluted again. A plateau of nucleic acid binding capacity is not reached, however, even with larger amounts of nucleic acid in the sample, and normalization did not occur even when using various amounts of starting DNA.

A) Reaction of Magnetic Polymers with Amines

Materials

Various materials can be used as magnetic polymer, including Estapor, Dynal, Seradyn or Ademtech particles.

Amine: N-propyl-1,3-propanediamine (Aldrich, Catalog No. 308153)

Instructions for Preparation

Resuspend 500 mg of carboxylated magnetic particles in 10 ml of MES buffer and then add 10 ml of 50 mg/ml solution of N-hydroxysuccinimide. Mix using a Minishaker, then add 10 ml of 50 µmol/l solution of 1-ethyl-3-(3-dimethylaminopropyl)carbodiimide and vortex again. Then leave to react for 30 minutes on the overhead shaker and then remove the supernatant. Resuspend in 50 ml of MES buffer. Separate the suspension magnetically and discard the supernatant. Then take up in 5 ml of MES buffer and add 10 ml of aqueous 1,4-diaminobutane solution (100 mg/ml in MES, pH 8.5), vortex thoroughly and leave to react for one hour on the overhead shaker. Next, wash twice with 50 ml of MES buffer each time, separate the supernatants magnetically and discard. Then resuspend the particles in 10 ml MES buffer.

B) Normalization of LR-PCR Fragments

1) Normalization of Different Amounts of Starting DNA of the Same Sample

Washing of the Beads:

4 batches: in each case wash 2 µl of beads with 2×100 µl of 50 mM TrisHCl pH6.5

The beads are concentrated in each case for at least 30 s on a magnet, before the supernatant is removed.

Binding of DNA:

Suspend the beads in 100 µl washing buffer (see above)+2 µl 3M NaAc pH5.3

1 +4 µl DNA LR-PCR06 (8 kb fragment)
2 +3 µl DNA LR-PCR06 +1 µl LR-PCR buffer 1×
3 +2 µl DNA LR-PCR06 +2 µl LR-PCR buffer 1×
4 +1 µl DNA LR-PCR06 +3 µl LR-PCR buffer 1×

Shake for 10 min at RT

Washing:

2× wash with 100 µl water

Elution:

+20 µl 50 mM Tris-HCl pH 8.5, 50 mM NaCl 5 min RT

Transfer the supernatants to fresh vessels.

Figure 2:
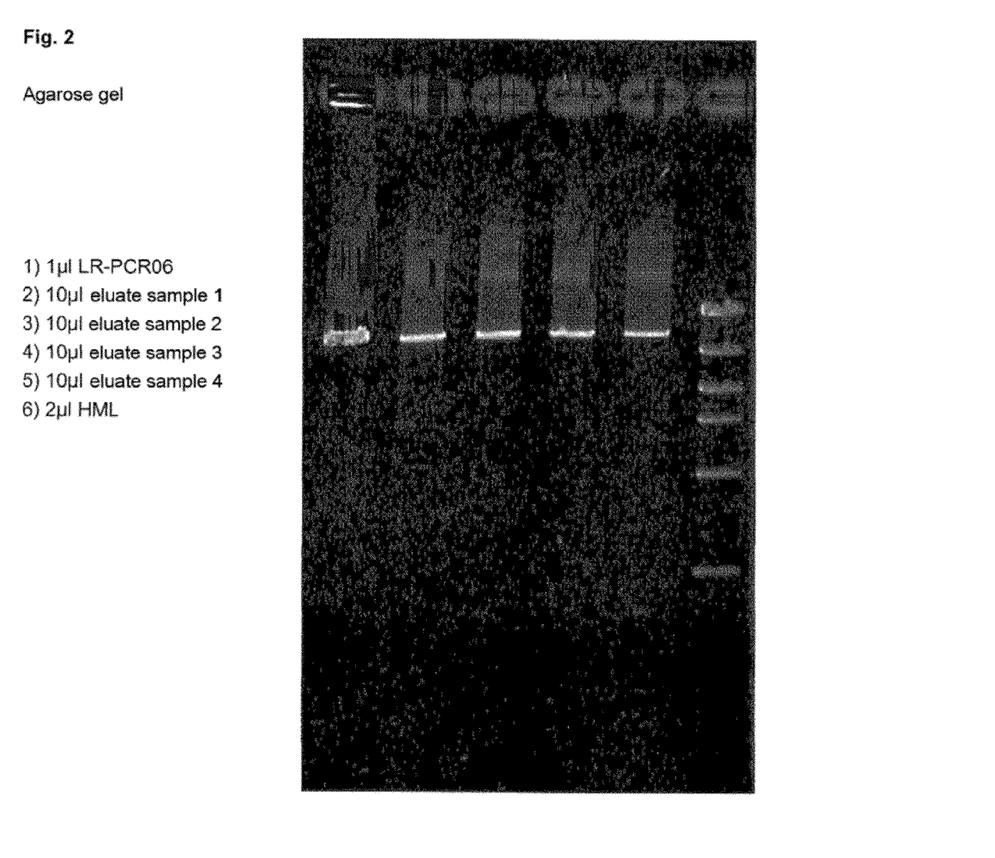
Figure 3:
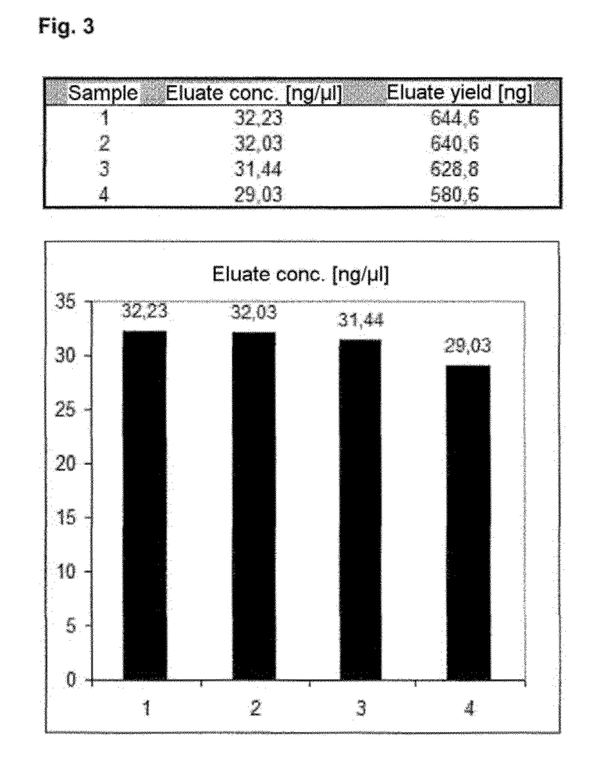

The results of normalization are presented in FIGS. 2 and 3.

Figure 4:
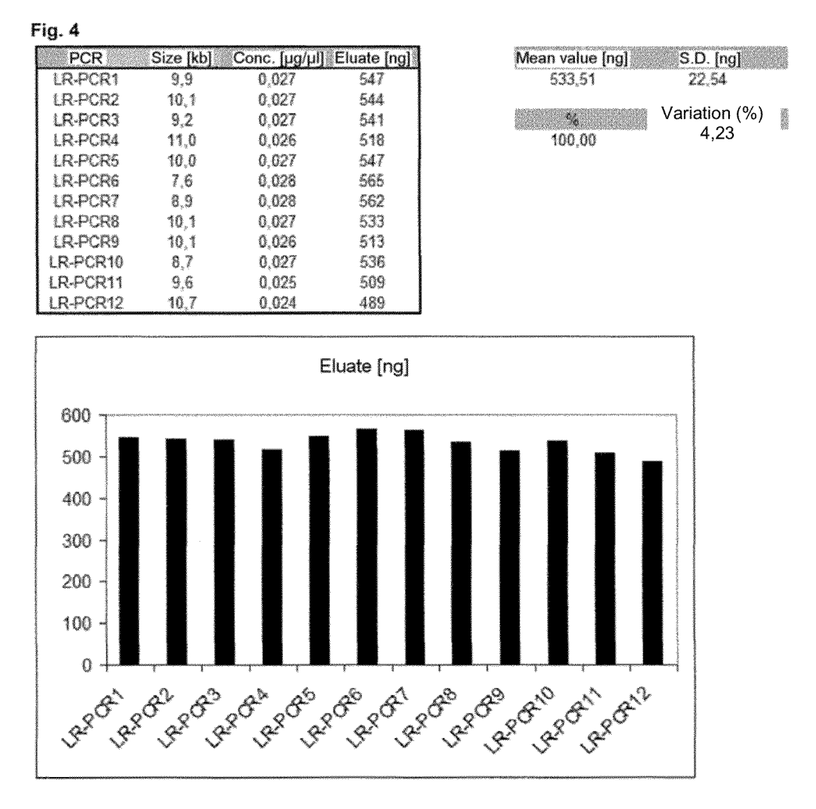

2) Normalization of Various DNA Fragments Between 8 and 11 kb 12 different long range PCR samples were purified and normalized according to the protocol in 1). FIG. 4 presents the amounts of DNA in the eluate after Pico-Green measurement.

Figure 5:
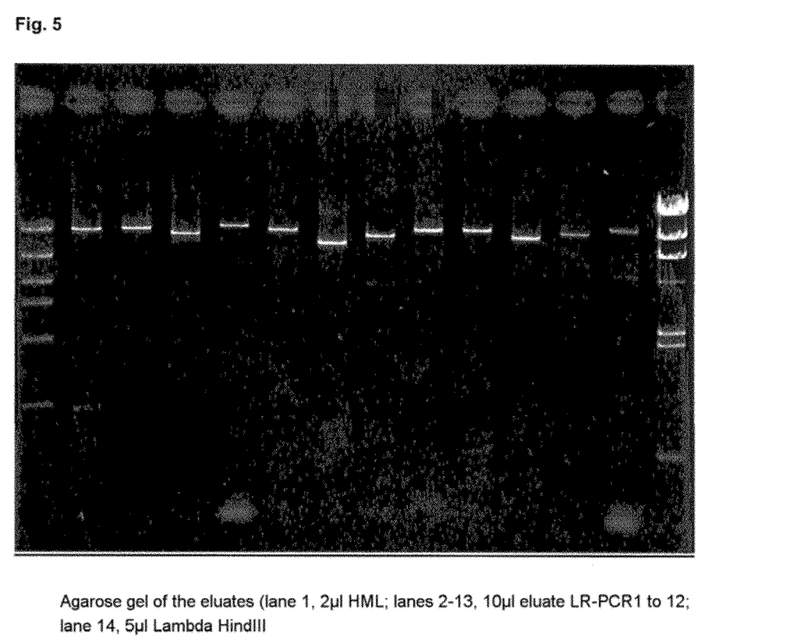

Then the 12 samples were combined and the average concentration was checked by $OD_{260nm}$ measurement. This gave an average value of 580 ng per PCR fragment, which is comparable to the average value of 533 ng from Picogreen measurement. The results are shown in FIG. 5. The weaker bands in lanes 12 and 13 can be explained by an increased DNA background, which was caused by nonspecific amplification.

It was shown in various tests that fragments of similar size (8-11 kb) and of different size (e.g. 1 kb, 5 kb, 10 kb; results not shown) could be normalized with small fluctuations of less than 10%. Therefore the method presented here represents a definite improvement over the existing known methods of normalization, whose fluctuations in yields are significantly larger, 50% or 2-3 times, respectively.

When the present method is used for normalization of PCR fragments, from knowledge of the fragment lengths, in addition to normalization of the DNA masses, normalization of the amounts of fragments (molarity) is also possible, using the formula $$\text{Volume } [\mu l] = MW \, [\mu g/\mu mol]/\text{conc } [\mu g/\mu l]$$

The method according to the invention therefore has considerable advantages over the prior art. Thus, a very good yield of 500 ng per 2 µl beads in 20 µl eluate is achieved, with fluctuations of only ±10%. The method according to the invention can be automated and can be used with magnetic separators, pipettes and shakers. Furthermore, it is particularly time-efficient, as 96 samples can be purified within 20 minutes in an automated process. This is a considerable advantage relative to the prior art, where purification of the same sample quantity sometimes takes 60 minutes or more.

C) Normalization of gDNA from Blood

1) Isolation of gDNA from Blood from Eight Different Donors

Materials

Sample: fresh whole blood from 8 different donors, EDTA stabilized.
Beads: 1 mg N-propyl-1,3-propanediamine-coated magnetic beads (see above)
Lysis buffer: 10 mM Tris, Triton X-100, pH 9.0
Binding buffer: 1.5 M potassium acetate pH 4.0
Washing buffer=water
Elution buffer: 10 mM Tris*HCl pH 8.5

Procedure:

Purification was carried out according to the following test instructions:

Mix together 1 ml lysis buffer and 10 µl proteinase K. Suspend 1 mg beads and 3.4 µl water in 200 µl binding buffer. In an Eppendorf vessel, add the lysis buffer/proteinase mix to 100 µl blood and mix well. Incubate at room temperature for 10 min. Carefully resuspend the beads in the binding buffer. Add 240 µl thereof to the lysed blood. Mix thoroughly by repeated pipetting. Incubate at room temperature for 1 min. Separate the beads magnetically. Carefully remove the supernatant. For washing, add 1 ml of washing buffer. Mix thoroughly by repeated pipetting. Separate again magnetically and discard the supernatant. Add 1 ml lysis buffer and 50 µl binding buffer, mix thoroughly and incubate at RT for one minute. Separate magnetically. Then wash once more with 1 ml washing buffer and separate magnetically.

For elution of the purified DNA, add 150 µl elution buffer to the beads. Resuspend the beads by repeated pipetting. Separate the beads magnetically, remove the supernatant and quantify the DNA photometrically.

Figure 6:
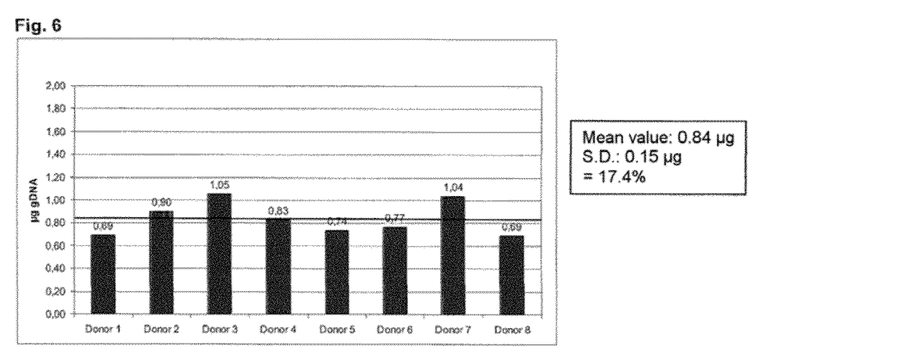

Result:

The results are shown in FIG. 6. The data show that although the starting materials used are very complex and can contain different amounts of nucleic acids, a normalized amount of DNA could be purified by the method according to the invention, which was subject to only slight fluctuations.

2) Isolation with Intentional Variation of the Starting Amount of DNA

In order to test whether the method according to the invention achieves DNA normalization even with complex samples, which contain very different amounts of DNA, the following test was carried out.

Materials

Sample: fresh whole blood, EDTA stabilized.
Beads: 600 µg N-propyl-1,3-propanediamine-coated magnetic beads
Lysis buffer: 10 mM TRIS, Triton X-100, pH 9.0
Binding buffer: 1.5 M potassium acetate pH 4.0
Washing buffer=water
Elution buffer: 10 mM TRIS*HCl pH 8.5

The theoretical starting amount of gDNA was determined by counting the white blood cells (WBC count=white blood cell count). 6.6 µg DNA was used per cell.

| Blood volume | WBC × $10^3/\mu l$ | Amount of DNA µg DNA |
|---|---|---|
| 50 µl | 4.7 | 1.55 |
| 100 µl | 4.7 | 3.10 |
| 150 µl | 4.7 | 4.65 |
| 200 µl | 4.7 | 6.20 |
| 250 µl | 4.7 | 7.76 |
| 300 µl | 4.7 | 9.31 |

Composition of the Lysis Mix:

| Blood volume | Proteinase K [µl] | Lysis buffer [ml] |
|---|---|---|
| 50 µl | 10 | 1 |
| 100 µl | 10 | 1 |
| 150 µl | 15 | 1 |
| 200 µl | 20 | 1 |
| 250 µl | 25 | 1 |
| 300 µl | 30 | 1 |

Procedure:

Purification was carried out according to the following test instructions:

In each case mix together the amounts of lysis buffer and proteinase K stated above. In each case suspend 600 µg beads (=16.9 µl) and 23.1 µl water in 200 µl binding buffer. In each case add the lysis buffer/proteinase mix to the above-stated amount of blood in an Eppendorf vessel and mix well. Incubate at RT for 10 min. Carefully resuspend the beads in the binding buffer. Add 240 µl thereof to the lysed blood. Mix thoroughly by repeated pipetting. Incubate at room temperature for 1 min. Separate the beads magnetically. Carefully remove the supernatant. For washing, add 1 ml of washing buffer. Mix thoroughly by repeated pipetting. Separate again magnetically and discard the supernatant. Add 1 ml lysis buffer and 50 µl binding buffer, mix thoroughly and incubate at RT for one minute. Separate magnetically. Then wash once more with 1 ml washing buffer and separate magnetically.

For eluting the purified DNA, add 150 µl of elution buffer to the beads. Resuspend the beads by repeated pipetting. Separate the beads magnetically, remove the supernatant and quantify the DNA photometrically.

Figure 7:
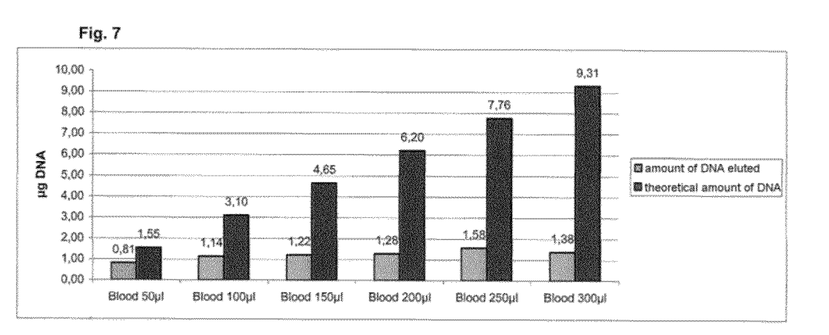

Result:

The results are shown in FIG. 7 and in the following table. The data show that although the starting materials used contained very different amounts of nucleic acids, a normalized amount of DNA could be purified by the method according to the invention, which was subject to far smaller fluctuations than the starting material.

| Mean value | S.D. | % |
|---|---|---|
| Input DNA: WBC | | |
| 5.43 | 2.90 | 53.45 |
| Output DNA: AX beads | | |
| 1.24 | 0.26 | 20.76 |

D.) Normalization of RNA
Materials:
Sample: RNA Boehringer Mannheim 16s- and 23s-ribosomal
β=4 µg RNA/µl
Beads: 38 µg N-propyl-1,3-propanediamine-coated magnetic beads
Bead washing buffer: 50 mM TRIS*HCl pH6.5 (RNase-free)
Binding buffer: 3 M sodium acetate pH5.3 (RNase-free)
Washing buffer=water (RNase-free)
Elution buffer: 50 mM TRIS*HCl/50 mM NaCl pH8.5 (RNase-free)
Amounts of RNA added: 1-8 µg (0.5 µg steps)
Volume of RNA added: 4 µl (volume differences made up with RNase-free water)
Procedure:

Purification was carried out according to the following test instructions:

Carefully resuspend the beads and put 38 µg in a microtiter plate. Magnetize, remove the buffer and take up the beads in 100 µl of bead washing buffer. Repeat this step once more. Then add 2 µl of binding buffer and 4 µl of the various RNA solutions. Mix thoroughly by repeated pipetting. Shake the plate for 10 minutes at 1000 rpm and room temperature (RT). Separate the beads magnetically. Carefully remove the supernatant.

For washing, add 100 µl of washing buffer. Mix thoroughly by repeated pipetting. Separate magnetically again and discard the supernatant. Repeat the washing step once more.

Figure 8:
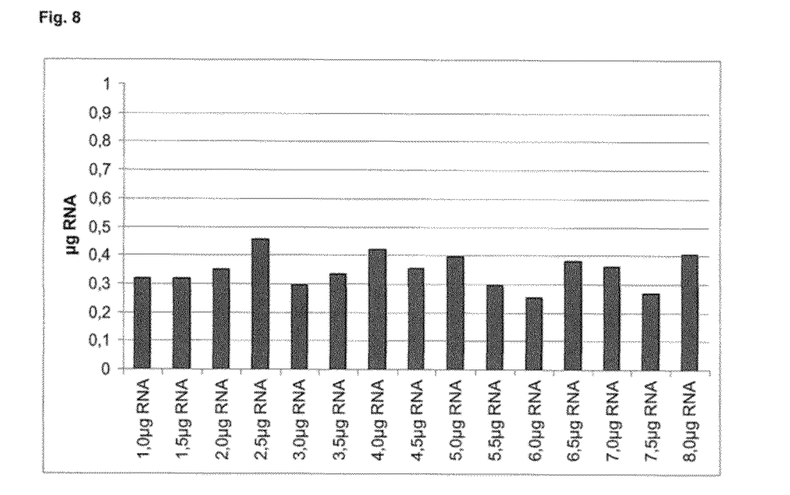

For elution of the RNA, add 20 µl of elution buffer to the beads. Resuspend the beads by repeated pipetting and shake for 5 minutes at 1000 rpm and RT. Separate the beads magnetically, remove the supernatant and quantify the RNA photometrically.
Result:

The results are shown in FIG. 8 and in the following table. The data show that although the starting materials used contained very different amounts of nucleic acids, a normalized amount of RNA could be purified by the method according to the invention, which was subject to far smaller fluctuations than the starting material.

| Mean value | S.D. | % |
|---|---|---|
| Input RNA 1.0-8.0 µg RNA | | |
| 4.5 | 2.236 | 50% |
| Output RNA: | | |
| 0.35 | 0.057 | 16% |

The invention claimed is:

1. A method for isolating and/or purifying a defined amount of nucleic acids from a nucleic acid-containing sample, the method having at least the following steps:

a. contacting the nucleic acid-containing sample with a defined amount of a nucleic acid binding phase with the following features:
  (i) the nucleic acid binding phase has nucleic acid binding ligands, which have at least one protonatable group;
  (ii) the nucleic acid binding ligands are bound to a carrier, wherein the low charge density is achieved by at least one of the following features:
    (aa) the nucleic acid binding ligands have, bound to the carrier, in each case not more than one or two protonatable groups for binding of the nucleic acids, and/or
    (bb) the nucleic acid binding ligands are selected from the group of mono- and diamines, and/or
    (cc) the carrier is coated with a mixture of nucleic acid binding ligands and diluting groups, wherein the proportion of nucleic acid binding ligands relative to the diluting groups is ≤50%; and/or
    (dd) the nucleic acid binding ligands bound to the carrier are in deficit, such that ≤50% of functional groups or groups functionalizable with nucleic acid binding ligands on the carrier are functionalized with nucleic acid binding ligands;
  (iii) the nucleic acid binding phase has a surface with a low charge density, wherein the amount of nucleic acids in the sample exceeds the binding capacity of the amount of nucleic acid binding phase used;
b. binding of the nucleic acids to the nucleic acid binding phase at a pH which is a binding pH that is below the pKs value of at least one of the protonatable groups;
c. elution of the nucleic acids at a pH that is above the binding pH, wherein a defined amount of nucleic acids is obtained.

2. The method according to claim 1, wherein at least one of said protonatable group(s) have at least one of the following features:
  a. a pKs value from 9 to 12;
  b. a pKs value from 10 to 12;
  c. the protonatable groups are amino groups and are not conjugated with the electron density-lowering groups.

3. The method according to claim 1, wherein the nucleic acid binding phase has at least one of the following features:
  a. the carrier and/or the nucleic acid binding ligands have functional groups that promote the release of the nucleic acids at the elution pH, optionally cation exchangers as functional groups, and optionally acid groups which are optionally carboxyl groups;
  b. the nucleic acid binding ligands are selected from the group consisting of primary, secondary and tertiary amines of the formulas
  $R_3N$, $R_2NH$, $RNH_2$ and/or $X-(CH_2)_n-Y$
  with
  $X=R_2N$, RNH or $NH_2$
  $Y=R_2N$ or RNH or $NH_2$
  R=independently of one another, a linear, branched or cyclic alkyl, alkenyl, alkynyl or aromatic substituent, wherein the latter can also contain one or more heteroatoms;
  n=0 to 20;
  c. the carrier has no nucleic acid binding properties of its own apart from the nucleic acid binding ligands;
  d. the carrier is selected from the group consisting of polystyrene and derivatives thereof, polyacrylates and polymethacrylates and derivatives thereof, polyurethanes, nylon, polyethylene, polypropylene, polybutylene and copolymers of these materials, agarose, cellulose, dextran, Sephadex, Sephacryl, chitosan, inorganic carriers, glass, metal oxides and metalloid oxides, $Al_2O_3$, $TiO_2$, silica, boron oxide, carriers with metal surfaces, gold and magnetic particles and mixtures thereof, tubes, membranes, fleece, paper, reaction vessels, multiplates, chips and microarrays; and/or e. the binding capacity is in the range from 0.1 to 500 µg nucleic acid per mg nucleic acid binding phase.

4. The method according to claim 1, wherein binding takes place under conditions that have at least one of the following features:
  a. binding takes place at a pH from 3 to 8; and/or
  b. binding takes place at a pH from 4 to 7.5; and/or
  c. binding takes place at a pH from 4.5 to 7; and/or
  d. binding takes place at a pH from 5.5 to 7; and/or
  e. binding takes place at a pH from 6.5 to 7; and/or
  f. binding takes place at a salt concentration of ≤1M, ≤0.5M, ≤0.25M or ≤0.1M.

5. The method according to claim 1, wherein elution takes place under conditions that have at least one of the following features:
  a. elution takes place at a pH that is above the binding pH, but at least one pH unit below the pKs value of at least one of the protonatable groups; and/or
  b. elution takes place at a pH from 7.5 to 10; and/or
  c. elution takes place at a pH from 8 to 9; and/or
  d. elution takes place at a pH from 8.2 to 8.8; and/or
  e. elution takes place at a salt concentration of ≤1M, ≤0.5M, ≤0.25M, ≤0.1M, ≤25 mM, ≤15 mM or ≤10 mM; and/or
  f. for elution, a solution is used that is selected from the group of water, biological and organic buffer.

6. The method according to claim 1, wherein a washing step is carried out after binding and prior to elution.

7. The method according to claim 6, wherein a washing solution is used that has at least one of the following features:
  a. water or an aqueous solution with low salt concentration is used for the washing step; and/or
  b. an aqueous solution with low salt concentration is used, wherein the salt concentration is ≤400 mM, ≤200 mM, ≤100 mM, ≤50 mM and/or ≤25 mM.

8. A nucleic acid binding phase recitable for isolating and/or purifying a defined amount of nucleic acids from a nucleic acid-containing sample, wherein the nucleic acid binding phase has nucleic acid binding ligands with at least one protonatable group, wherein the nucleic acid binding ligands are bound to a carrier and the nucleic acid binding phase has a surface with a low charge density, wherein the low charge density is achieved by at least one of the following features:
  a. the nucleic acid binding ligands have, bound to the carrier, in each case not more than one or two protonatable groups for binding the nucleic acids; and/or
  b. the nucleic acid binding ligands are selected from the group of mono- and diamines; and/or
  c. the carrier is coated with a mixture of nucleic acid binding ligands and diluting groups, wherein the proportion of nucleic acid binding ligands relative to the diluting groups is ≤50%; and/or
  d. the nucleic acid binding ligands bound to the carrier are in deficit, such that ≤50% of functional groups or groups functionalizable with nucleic acid binding ligands on the carrier are functionalized with nucleic acid binding ligands;
wherein an elution pH is established that is above the binding pH and wherein the amount of nucleic acid binding phase is selected so that the nucleic acids in the sample are in excess to the binding capacity of the nucleic acid binding phase used.

9. The nucleic acid binding phase according to claim 8, wherein the nucleic acid binding phase has at least one of the following features:
  a. the protonatable group(s) have a pKs value from 9 to 12; and/or
  b. the protonatable groups are amino groups and are not conjugated with the electron density-lowering groups; and/or
  c. the nucleic acid binding phase has functional groups that promote the release/elution of the nucleic acids at the elution pH, the functional groups optionally being cation exchangers, optionally being carboxyl groups; and/or
  d. the binding capacity of the nucleic acid binding phase is in the range from 0.1 to 500 µg nucleic acid per mg nucleic acid binding phase;
  e. the carrier has no nucleic acid binding properties of its own apart from the nucleic acid binding ligands; and/or
  f. the carrier is selected from the group consisting of polystyrene and derivatives thereof, polyacrylates and polymethacrylates and derivatives thereof, polyurethanes, nylon, polyethylene, polypropylene, polybutylene and copolymers of these materials, agarose, cellulose, dextran, Sephadex, Sephacryl, chitosan, inorganic carriers, glass or further metal oxides and metalloid oxides, $Al_2O_3$, $TiO_2$, silica, boron oxide, carriers with metal surfaces, gold, magnetic particles or mixtures thereof, tubes, membranes, fleece, paper, reaction vessels, multiplates, chips and microarrays; and/or
  g. the nucleic acid binding ligands are selected from the group consisting of primary, secondary and tertiary amines of the formulas
  $R_3N$, $R_2NH$, $RNH_2$ and/or $X—(CH_2)_n—Y$
  with
  $X=R_2N$, RNH or $NH_2$
  $Y=R_2N$ or RNH or $NH_2$
  R=independently of one another, a linear, branched or cyclic alkyl, alkenyl, alkynyl or aromatic substituent, wherein the latter can also contain one or more heteroatoms;
  n=0 to 20.

10. A kit for isolating and/or purifying a defined amount of nucleic acids from a nucleic acid-containing sample, wherein said kit comprises a nucleic acid binding phase as defined in claim 8.

11. The kit according to claim 10, comprising at least one of the following features:
  a. a binding buffer or a binding solution with a pH that is at least one pH unit below the pKs value of at least one of the protonatable groups of the nucleic acid binding phase, and/or a binding buffer or a binding solution that enables the adjustment of said pH in the sample; and/or
  b. an elution buffer or an eluting solution with a pH that is one pH unit below the pKs value of at least one of the protonatable groups of the nucleic acid binding phase, and/or an elution buffer or an eluting solution that enables the adjustment of said pH in the sample.

12. The kit according to claim 10, wherein
  a. the binding buffer or the binding solution has at least one of the following features:
    i. a pH from 3 to 8; and/or
    ii. a pH from 4 to 7.5; and/or
    iii. a pH from 4.5 to 7; and/or
    iv. a pH from 5.5 to 7; and/or
    v. a pH from 6.5 to 7; and/or
    vi. a salt concentration of ≤1M, ≤0.5M, ≤0.25M or ≤0.1M;

and/or
  b. the elution buffer or the eluting solution has at least one of the following features:
     i. a pH from 7.5 to 10; and/or
     ii. a pH from 8 to 9; and/or
     iii. a pH from 8.2 to 8.8; and/or
     iv. a salt concentration of ≤1M, ≤0.5M, ≤0.25M, ≤0.1M, ≤25 mM, ≤15 mM or ≤10 mM; and/or
     v. it is selected from the group consisting of water, biological and organic buffer.

13. The method of claim 9, wherein the nucleic acid binding phase is a polymer particle modified with N-propyl-1,3-propanediamine.

14. The method according to claim 1, wherein the method is carried out following a classical nucleic acid purification technique, in order to normalize already purified nucleic acids and obtain a defined amount of nucleic acids.

15. The method according to claim 1, wherein the normalized nucleic acid is used for an enzymatic reaction, a modification reaction, or a sequencing reaction.

16. The method of claim 15, wherein said enzymatic reaction is a nucleic acid amplification reaction.

17. The method according to claim 1, wherein the nucleic acid is a PCR fragment.

* * * * *